(12) United States Patent
Burton

(10) Patent No.: US 8,075,488 B2
(45) Date of Patent: Dec. 13, 2011

(54) ULTRASOUND DIAGNOSIS AND TREATMENT APPARATUS

(75) Inventor: David Burton, Camberwell (AU)

(73) Assignee: Compumedics Medical Innovation Pty. Ltd., Abbotsford, Victoria (AU)

( * ) Notice: Subject to any disclaimer, the term of this patent is extended or adjusted under 35 U.S.C. 154(b) by 1189 days.

(21) Appl. No.: 11/813,672

(22) PCT Filed: May 12, 2006

(86) PCT No.: PCT/AU2006/000620
§ 371 (c)(1),
(2), (4) Date: Jul. 10, 2007

(87) PCT Pub. No.: WO2006/119572
PCT Pub. Date: Nov. 16, 2006

(65) Prior Publication Data
US 2008/0132790 A1    Jun. 5, 2008

(30) Foreign Application Priority Data
May 12, 2005    (AU) ................................. 2005902400

(51) Int. Cl.
*A61B 8/00* (2006.01)
(52) U.S. Cl. .......................................................... 600/454
(58) Field of Classification Search .................... 600/454
See application file for complete search history.

(56) References Cited

U.S. PATENT DOCUMENTS

| | | | |
|---|---|---|---|
| 3,735,755 A | 5/1973 | Eggleton | |
| 5,379,770 A | 1/1995 | Van Veen | |
| 5,409,005 A | 4/1995 | Bissonnette et al. | |
| 5,844,140 A | 12/1998 | Seale | |
| 5,951,476 A | 9/1999 | Beach | |
| 6,186,949 B1 | 2/2001 | Hatfield et al. | |
| 6,547,737 B2 | 4/2003 | Njemanze | |

FOREIGN PATENT DOCUMENTS

| | | |
|---|---|---|
| WO | 89/07907 A1 | 9/1989 |
| WO | 00/49946 A1 | 8/2000 |
| WO | 01/32258 A2 | 5/2001 |
| WO | 01/69283 A2 | 9/2001 |
| WO | 2004/103184 A2 | 12/2004 |

*Primary Examiner* — Brian Casler
*Assistant Examiner* — Jonathan Cwern
(74) *Attorney, Agent, or Firm* — Scott H. Davison; Procopio, Cory, Hargreaves & Savitch LLP

(57) ABSTRACT

The invention provides apparatus and methods for semi-automatic or automatic imaging or treatment of occlusions in vessels using pulsed or unpulsed focussed sound waves, preferably ultrasound, in Doppler technology. The apparatus comprises at least one sound transducer member including at least one sound-emitting element for producing at least one sound wave beam; means to adjust the parameters of said at least one sound wave beam; means to spatially locate said at least one sound-emitting element; means to move said at least one transducer member; means to control movement of said at least one transducer member automatically or semi-automatically; means to automatically or semi-automatically focus sound waves generated by said at least one sound-emitting element into a beam; and means to accept sound signals from sound-emitting element or elements. The invention provides method for semi-automatically or automatically locating an occlusion in a vessel, including the steps of identifying regions of a body in which emboli might be found are identified; selecting a region of interest for sonication; sonicating the region of interest with at least one sound wave beam by moving said sound beam across the region of interest; receiving reflected sound signals from the region of interest; and calculating the Doppler effect parameters of flow and turbulence from said reflected sound signals.

50 Claims, 9 Drawing Sheets

Figure 2a

Near-field lengths and far-field divergence
of commercially available transducers

| Transducer diameter (mm) | Frequency (MHz) | Near-field length (cm) | Far-field divergence |
|---|---|---|---|
| 8 | 10 | 10.4 | 1"21' |
| 8 | 5 | 5.2 | 4"25' |
| 12 | 2.5 | 1.1 | 1"48' |
| 12 | 5.0 | 11.7 | 1"48' |
| 15 | 1.0 | 9.1 | 2"52' |
| 20 | 1.0 | 6.5 | 5"23' |

Figure 2b

Approximate Velocities of
Ultrasound In Selected Material

| Material | Velocity (m/sec) |
|---|---|
| Fat | 1.475 |
| Brain | 1.560 |
| Liver | 1.570 |
| kidney | 1.560 |
| Spleen | 1.570 |
| Blood | 1.570 |
| Muscle | 1.580 |
| Lens of Eye | 1.620 |
| Skull Bone | 3.360 |
| Soft Tissue (Mean Value) | 1.540 |
| Air | 331 |

Figure 9a

Pulse rate

- Number of separate pulses that are produced each second
- Remember – the transducer must act as a transmitter and a receiver
- Common pulse rate for abdominal imaging is 1,000 pulses/second
- Different and unrelated to frequency

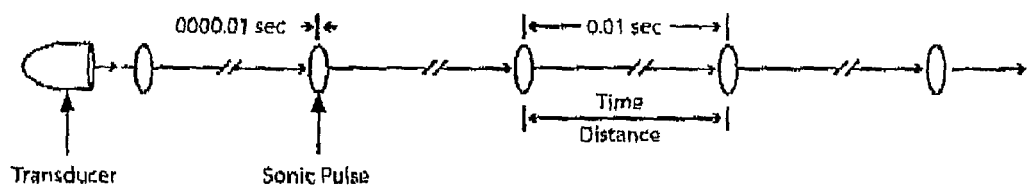

Figure 9b

Depth (axial) Resolution

This figure shows a time sequence
of an ultrasonic pulse resolving two surfaces,
a and b, separated by $X$ distance

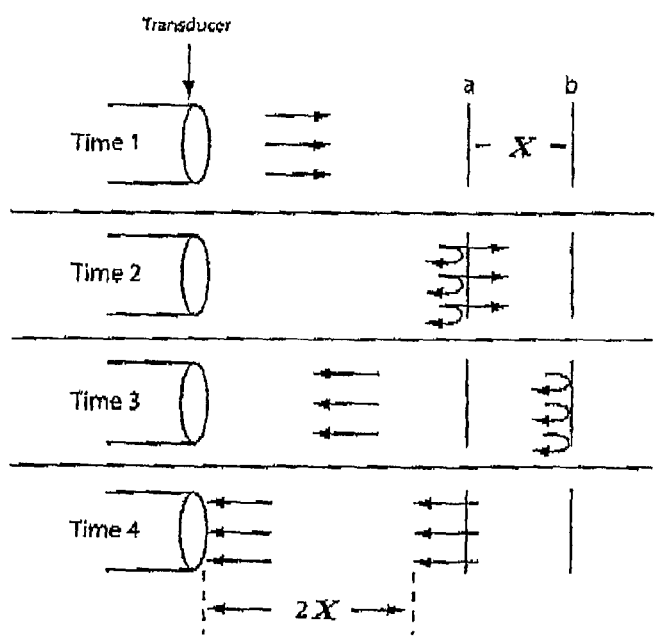

ULTRASOUND DIAGNOSIS AND TREATMENT APPARATUS

FIELD OF THE INVENTION

This invention relates to apparatus for the generation of sound waves, in particular to apparatus for transcranial Doppler sound devices for medical treatment of patients suffering from blood vessel occlusions or restriction in the brain characteristic of a stroke.

BACKGROUND

Blood circulation through the body is essential for maintenance and growth of calls and tissues. Any condition that restricts blood flow can have mild to disastrous consequences. For example, when blood flow in the brain is impeded, stroke can result. Stroke is a medical affliction that has severe consequences for most people who suffer it. Stroke is classified into four types, two of which are caused by blood clots (ischaemic stroke) and two of which are caused by haemorrhage (haemorrhagic stroke). Cerebral thrombosis and cerebral embolism account for up to 80 percent of all strokes.

Treatment options for stroke are limited. For example, only tissue plasminogen activator (tPA) has been approved, by the United States Food and Drug Administration as a pharmaceutical therapeutic treatment for ischaemic stroke.

It has been shown that the use of ultrasound waves and the Doppler frequency shift can be used to monitor the flow of blood through vessels (eg. Tegeler and Ratanakorn, 1999). Apparatus have been developed to exploit the potential of ultrasound to locate the interface between tissue types in the body, in particular, in the head, using transcranial Doppler ultrasound technology (TCD). U.S. Pat. No. 4,817,621 described apparatus to locate reliably blood vessels in the brain and to determine blood flow through vessels in the head using TCD. The apparatus relied on the combination of two parallelogram-like linkage systems to support and locate an ultrasound transducer near the head of a patient to locate occluded blood vessels in the brain using TCD. More recently, it has been shown that monitoring of patients with TCD, in addition to treatment with tPA may increase the effectiveness of tPA in the treatment of ischaemic stroke (Alexandrov et al. 2004), using commonly available TCD devices and operators skilled in using the devices to locate occlusions.

Transcranial Doppler technology has been shown to be useful in the identification and treatment of small vessel knock (WO2004/103184) associated with small vessel occlusion leading to stroke. The treatment taught in WO2004/103184 requires significant effort by an operator to find and diagnose the occluded blood vessels characteristic of stroke. While it has been shown that currently available ultrasound transducers and systems may be used for monitoring occluded blood vessels in stroke might also be a beneficial treatment method alleviating the symptoms of stroke, the ability to use TCD as a therapeutic treatment is currently constrained by the ease of use of said currently available systems. Clinicians who have used currently available TCD systems have noted that vascular tests that require the use of said TCD systems are among the most difficult to perform (Alexandrov et al., 2004). The ability of clinicians to diagnose and treat stroke with the promising TCD ultrasound technology may be limited by the apparatus with which to diagnose and treat the condition. For example, the current method of identifying the presence of occlusions in brain blood vessels is a manual grading system, known as the thrombolysis in brain ischaemia (TIBI) flow grading system. One of the problems with a head cap or band mounted or any other body or head mounted automatic diagnostic or treatment ultrasound device is that stability of movement of the sensor with patient movement or simply device attachment slippage can affect measures and data integrity.

What is needed is an apparatus and method to more efficiently locate occluded blood vessels or vessels having restriction in the brain characteristic of stroke and to treat the occlusions or restrictions to alleviate the stroke symptoms.

In this document the words "including" and "comprising" are used interchangeably and with the same meaning, which is intended to indicate non-limiting incorporation of elements.

BRIEF DESCRIPTION OF THE FIGURES

FIG. 2a shows a table of data providing near-field lengths and far-field divergence of ultrasound waves generated by typical ultrasound transducers.

FIG. 2b shows a table of data showing the variation in velocity of ultrasound waves through selected materials found in living organisms.

FIG. 9a shows an example of the pulse rate of an ultrasound transducer.

FIG. 9b shows and example of depth resolution of an ultrasound transducer.

SUMMARY OF THE INVENTION

Figure 1:
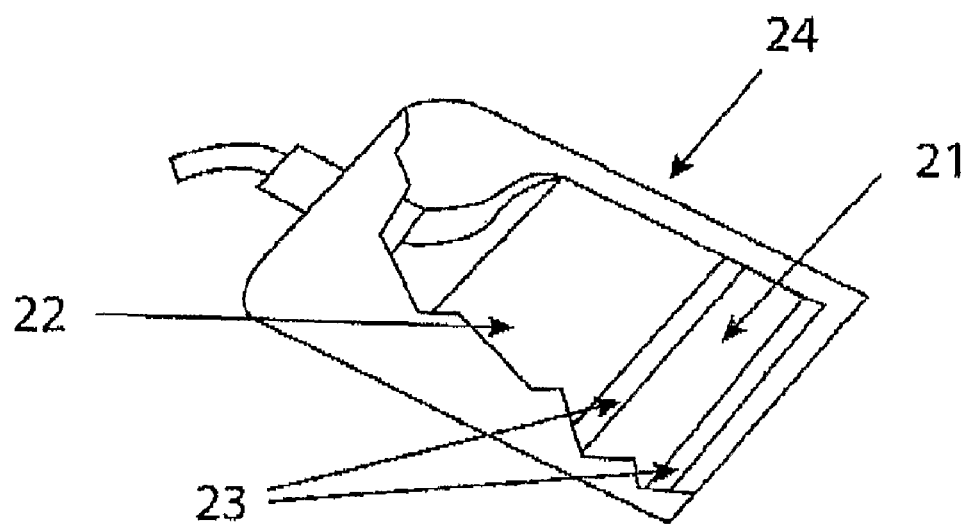
FIG. 1 shows an embodiment of an ultrasound transducer useful in the invention.

In one aspect the invention provides apparatus for imaging or treatment of restrictions or occlusions in vessels using sound waves, comprising at least one sound transducer member including at least one sound-emitting element for producing at least one sound-wave beam; means to adjust the parameters of said at least one sound-wave beam; means to spatially locate said at least one sound-emitting element; means to automatically or semi-automatically focus sound waves generated by said at least one sound-emitting element into a beam, and means to accept sound signals from sound-emitting element or elements. Preferably the apparatus includes means to move said at least one transducer member and means to control movement of said at least one transducer member automatically or semi-automatically. Preferably the sound-emitting element and the means to accept sound signals are the same. Preferably the at least one sound-wave beam is pulsed. Preferably the at least one sound-wave beam is focussed electronically. The invention may include two or more sound-emitting elements forming an array and the array may be curved. The at least one sound-wave beam may incorporate a plurality of frequencies of sound waves in combinations of concurrent frequencies generated by the sound-emitting elements in the array or in a series of frequencies over time. The array may be comprised of sound-emitting elements in any of fixed position, adjustable position, or scanning position. The apparatus may include fiducial registration means and communication mean for communicating the position of the at least one sound-emitting element and maintaining the at least one sound-emitting element in optimal positioning during sonication.

In another aspect, the invention provides apparatus for imaging or treatment of restrictions or occlusions in vessels using sound waves, comprising at least one sound-wave transducer member including at least one sound-emitting element for producing at least one sound-wave beam; means to adjust the parameters of said at least one sound-wave beam; means to orient said at least one transducer member; means to focus sound waves generated by said sound-emitting element into a beam; and means to accept sound signals from sound-emitting element or elements. The sound-emitting elements may be moveable singly or in a coordinated manner, including simultaneously. The sound-emitting elements may be servo-controlled, including feedback control. The servo-control means may be self-tracking and include means for determining out-of-range positioning of said at least on sound-emitting element. The feedback control may Incorporate a signal characteristic of an occlusion in a fluid flow. The apparatus may include a plurality of sound-emitting elements in at least two layers of at least two arrays. Preferably each transducer member is operable to enable a continuously adjustable focus point comprising of two or more sound beams emitted by at least two sound-emitting elements. Preferably the apparatus includes means to transform sound signals from analogue to digital forms or digital to analogue forms. Preferably the apparatus includes means to store transformed digital data. Preferably the apparatus includes means to display analogue or digital data. Preferably the apparatus includes video display means for displaying data. The apparatus may include voice coil control means. Preferably the apparatus is operable in real-time or near real time. Preferably the apparatus includes fiducial registration means for maintaining targeted sonication. Preferably the apparatus is used for detecting and sonicating vessels in the brain of a being. Preferably the sound waves are ultrasound waves.

In another aspect, the invention provides a method for locating an occlusion or restriction in a vessel, including the steps of identifying regions of a body in which an occlusion or restriction in a vessel might be found; selecting a region of interest for sonication; sonicating the region of interest with at least one sound-wave beam by moving said at least one sound-wave beam across the region of interest; receiving reflected sound signals from the region of interest; and calculating the Doppler effect parameters of flow and turbulence from said reflected sound signals.

In another aspect, the invention provides a method for distinguishing anatomical features of an organism including the steps of sonicating a region of interest in a subject with at least one sound-wave beam, whereby the frequency of said at least one sound-wave beam is suitable for determining a particular tissue type, receiving reflected sound signals from said region of interest, calculating the Doppler effect parameters of said reflected sound signals and characterising said Doppler effect parameters according to parameters associated with known tissue types.

The method of the invention may include the step of modifying the characteristics of the at least one sound-wave beam to target a region of interest wherein the Doppler effect parameters are indicative of reduced flow attributable to an occlusion or a restriction. The method may include the step of sonicating the region of interest thereby causing agitation or dissipation of the occlusion by prolonged sonication or recanalisation of a restriction. The method may include the step of automatically or semi-automatically evaluating and optimising the effect of sonication on an occlusion for feedback modification of said at least one sound-wave beam, said evaluating and optimising including tissue safety guidelines. The method may include that the step of automatically or semi-automatically evaluating and optimising the effect of sonication includes maintaining a fiducial registration between sound waves beams and a registration signal. The method may include the step of calculating and displaying any one or a combination of an index, measure, or marker or suitable representation indicating the progress of dissipation of an occlusion in a vessel or recanalisation of a vessel having an occlusion or restriction. The method may be carried out automatically or semi-automatically substantially without human control. The method may be carried out wherein the region of the body is the head. Preferably the region of the head is the circle of Willis. The method may include the two or more sound-wave beams moving across said region of interest in either a simultaneous or sequential manner. The method may include having the at least one sound-wave beam pulsed. The method may include the parameters calculated from said reflected sound signals being any one or a combination of power, spectral, amplitude, phase coupling or frequency characteristics characteristic of a spatial representation of anatomical features in said region of interest or occlusive material. Preferably the power or amplitude spectral analysis are carried out using Fast Fourier Transform techniques. Preferably the at least one sound-wave beam is continuous. The method may include the at least one sound-wave beam being initially transmitted with a first frequency or amplitude and subsequently with periodic changes resulting a second and further frequency or frequencies or amplitude(s) relative to the first beam frequency so that the mark-to-space ratio of the apparent changing and pulse formation is continuous. Preferably the sound-wave beam is comprised of ultrasound waves. The method may include the step of conducting a spatial voxelated analysis of received signals.

DETAILED DESCRIPTION OF THE DRAWINGS AND PREFERRED EMBODIMENTS

It is an object of the present invention to provide an apparatus that reduces the need for significant operator interaction with a sound-wave generating device used in the identification and treatment of embolism or stenosis. It is a further object of the invention to provide a method of semi-automatic or automatic location of embolism or stenosis using sound waves. It is a further object of the invention to provide an apparatus for the automatic or semi-automatic location of blood vessel emboli or stenosis in the brain. It is a further object of the invention to provide a means to semi-automatically or automatically locate an occlusion or restriction in a blood vessel. It is a further object of the invention to provide a means to semi-automatically or automatically treat said emboli or occlusion or restriction with sound waves. It is a further object of the invention to provide an apparatus to utilise the energy of transcranial Doppler ultrasonography in thrombolysis and recanalisation of blood vessels in the brain.

The following description refers to the preferred embodiment of the invention using ultrasound waves. It will be understood that sound waves of other frequencies than ultrasound are suitable for other embodiments within the scope of the invention. For example, in another embodiment, the invention includes apparatus that utilises low-frequency pulsatile sound waves that may be focussed to achieve similar results as the preferred ultrasound waves. In this document, the word, "occlusion", includes any one of, or a combination of, an embolism, thrombus, or other biological matter, non-biological matter, including gases, from whatever source. In this document, the word, "stenosis", includes any restriction in a fluid-containing vessel.

An example transducer member 24 comprising a single ultrasound-emitting element is illustrated in FIG. 1, the ultrasound-emitting element includes a piezoelectric element 21, backing material 22, and electrodes 23. The ultrasound-emitting element converts electric voltage applied across the ultrasound-emitting element into ultrasonic sound-wave energy. When a beam of ultrasonic sound-wave energy is directed toward heterogeneous biological material of interest, the ultrasonic sound-wave energy is reflected at the interfaces of biological structures within the biological material. The reflected energy causes an ultrasound-receiving element to vibrate and to produce a voltage signal which can be processed to decipher the reflective properties of the biological material. It will be understood by persons skilled in the art that a single ultrasound element may function either as an ultrasound-emitting element, an ultrasound-receiving element, or both an ultrasound-emitting and an ultrasound-receiving element. An ultrasound beam produced by an ultrasound-emitting element may be pulsed or unpulsed in duration. A pulsed beam is pulsed at a rate required for the biological material of interest as illustrated in FIG. 9a. FIG. 9b shows the time sequence of an ultrasound beam resolving two surfaces. It will be understood that axial or depth resolution is the ability to determine the axial resolution of two objects located tandem to the ultrasonic beam. The axial resolution is determined by the spatial pulse length.

The transducer diameter can be selected to suit various depth ranges required for different treatment applications. FIG. 2a shows the properties of a range of depths of commercially available ultrasound transducers and FIG. 2b shows the variability of velocity of ultrasound beams in different biological materials, which is exploited in the invention. The velocity of the ultrasound signal depends on the constitution of the material through which the signal travels, the velocity being directly proportional to the density through which the ultrasound is transmitted. The transmission through tissue is 1540 m sec$^{-1}$ or, alternatively, a 1 cm transmission depth requires 13 μsec to be traversed by an ultrasound wave.

Figure 3A:
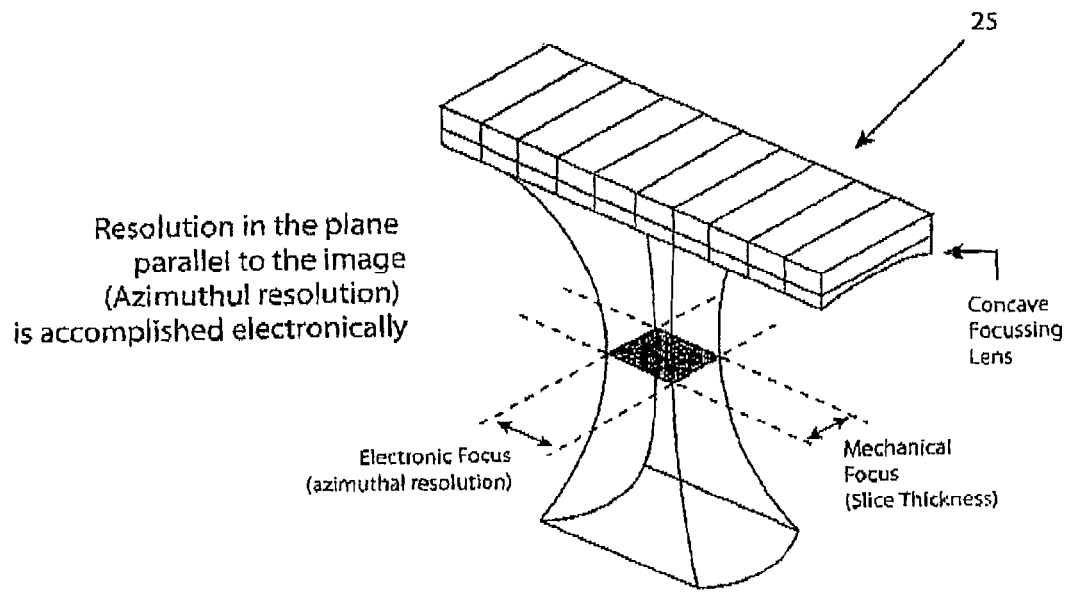
FIG. 3a shows an embodiment of multiple ultrasound transducers focussed electronically.
Figure 3B:
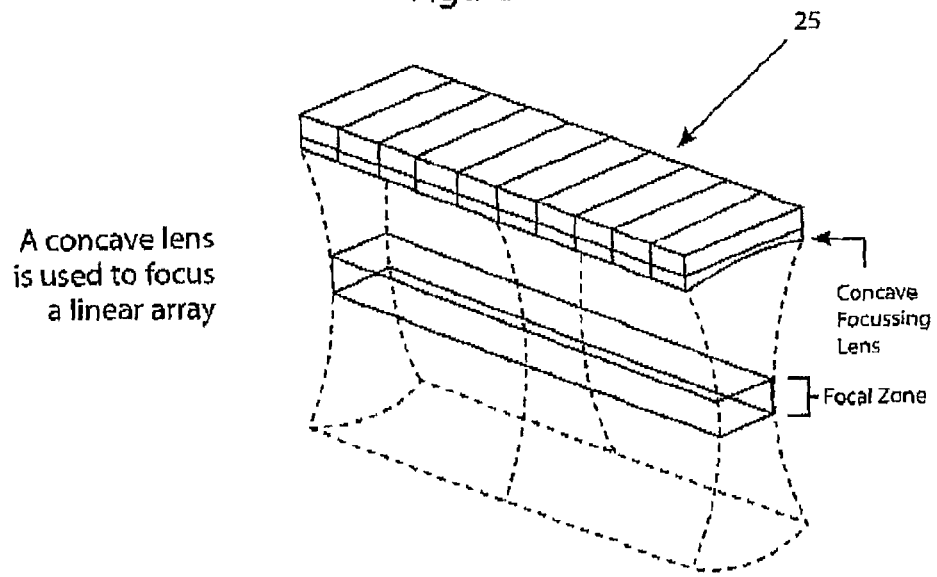
FIG. 3b shows an embodiment of a concave lens being used to focus a linear array of ultrasound transducers.
Figure 8A:
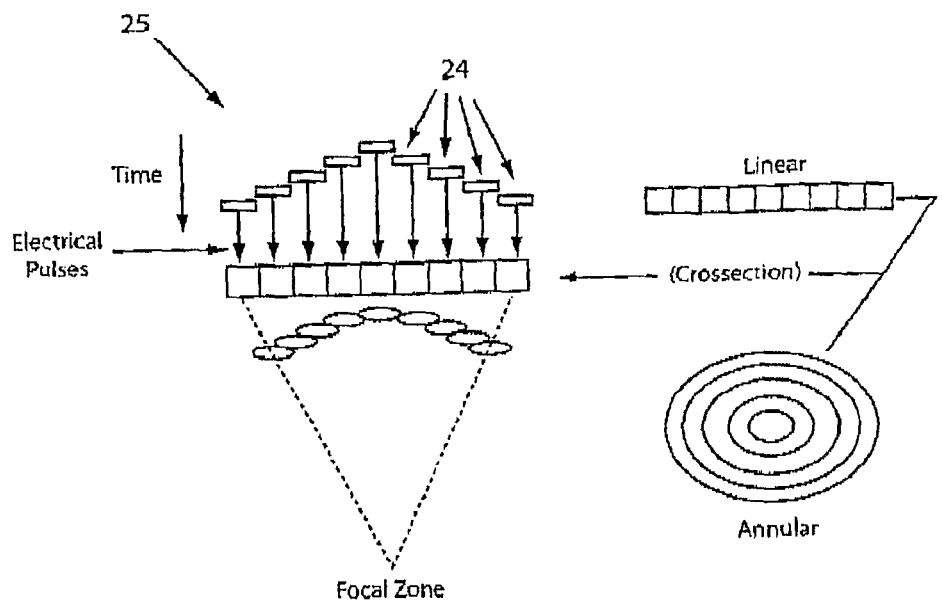
FIG. 8a shows an example of electric focussing of an ultrasound transducer.
Figure 8B:
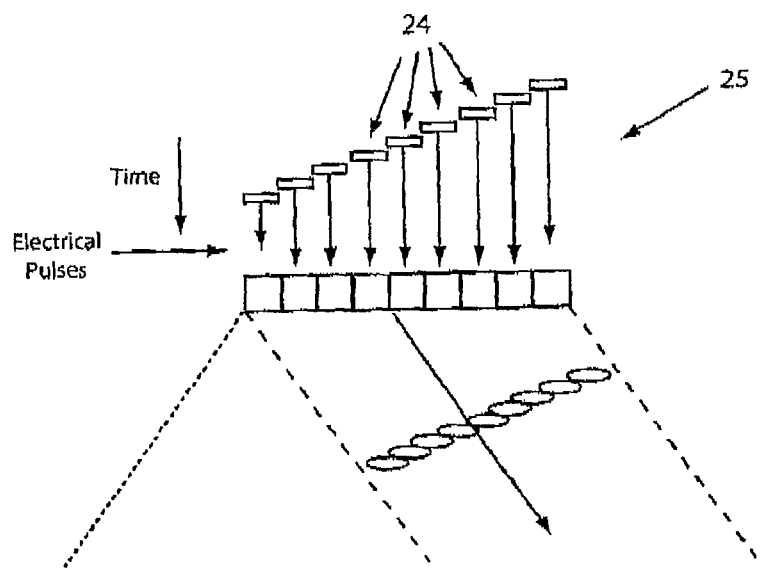
FIG. 8b shows an example of a phased array of ultrasound transducers.

The ultrasonic beams generated by a transducer can be focussed with focussing means. Preferably the lateral and depth positioning of the ultrasonic beam focus point can be adjusted by way of electronic focussing, illustrated in FIG. 8a. An embodiment of a focussed transducer member 25 with an ultrasound-emitting element, shown in FIG. 3a, can provide improved lateral resolution at depth. Focussing types can include curved mirrors, acoustic crystals, acoustic lens, or phased array (employing electronic focussing). The operation of ultrasound-emitting elements in a phased array is shown in FIG. 8b.

Figure 4:
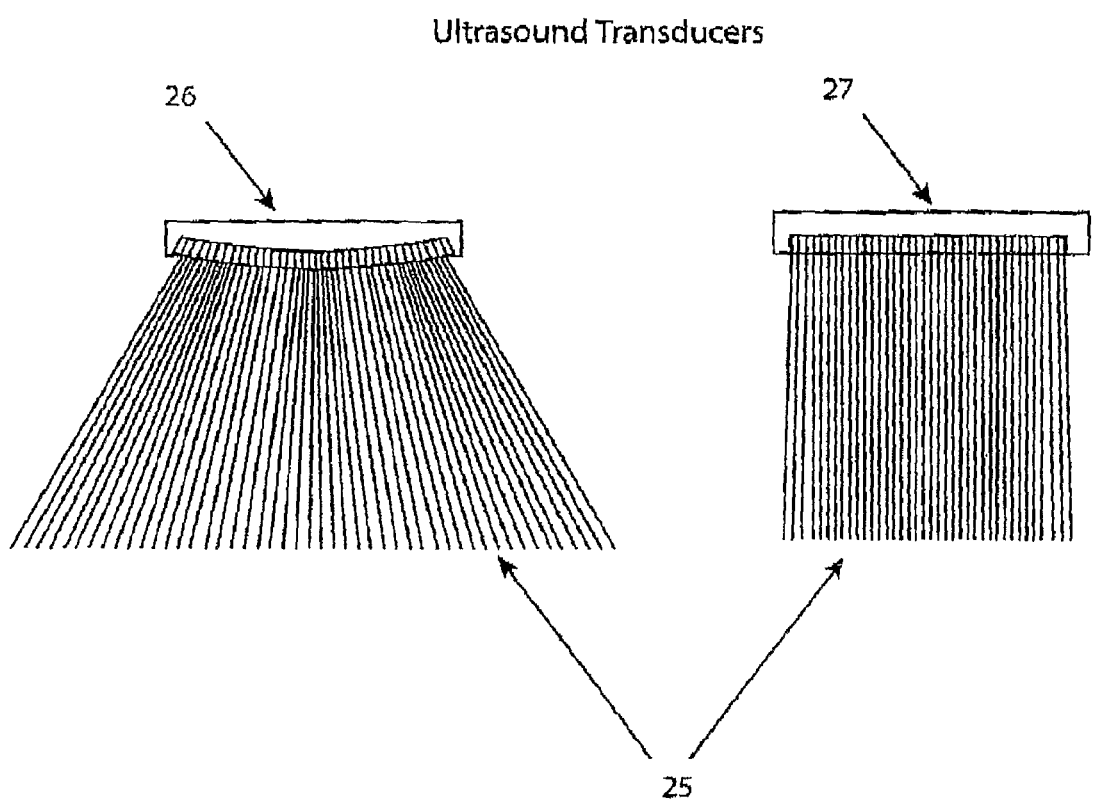
FIG. 4 shows embodiments of arrays of transducers, including curved and linear arrays.
Figure 5:
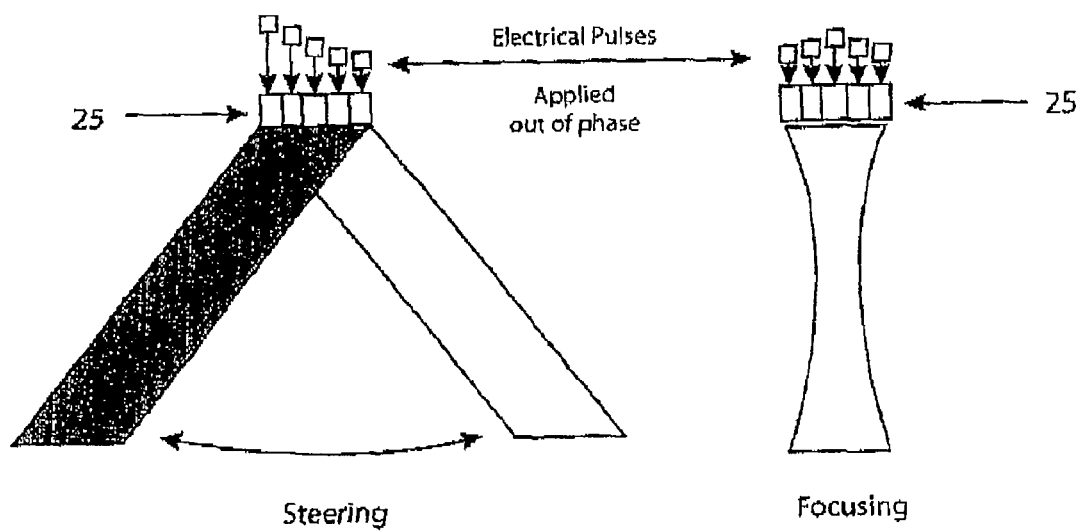
FIG. 5 shows embodiments of phased arrays of transducers which can be steered and focussed electronically.

The ultrasound-emitting elements may be positioned in an array within a transducer member 25 and may take alternative forms. FIG. 4 shows that such forms may include curved arrays 26 and linear arrays 27. The application of voltage to an array of ultrasound-emitting elements of a transducer member may be pulsed out-of-phase to achieve steering and focussing of an ultrasound beam as illustrated in FIG. 5. The invention includes that each of said at least one transducer members 25 may be comprised of any combination of ultrasound-emitting and receiving elements.

Figure 6:
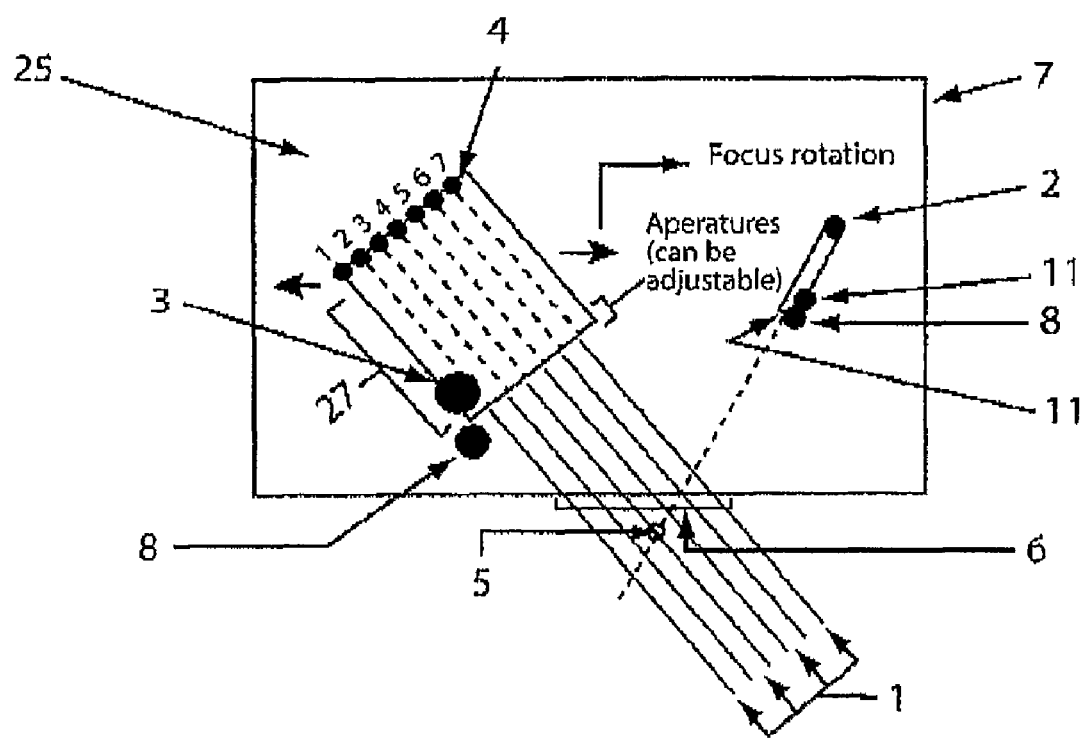
FIG. 6 shows an embodiment of the invention as an adjustable servo-array of ultrasound transducers.

Illustrated in FIG. 6 is an embodiment of the invention. It will be understood that a particular embodiment will incorporate a selection of features to achieve the objects of the invention and that the embodiment in FIG. 6 is illustrative only. A sensor enabling said ultrasonic-beam transmission and/or handling may be comprised of piezo or PVD material, or other suitable material or a suitable sensor capable of generating and/or receiving ultrasonic beam signals. Said at least one transducer member may include a combination of one or more members in fixed-position array, adjustable-position array 1, scanning-position single-member 2 or multiple-element transducer members, fixed-position single-member or multiple-element transducer members.

The focussing point 5 of an ultrasonic beam can be achieved through any combination of servo-driven control of an adjustable-position array-transducer member 3, servo-driven control of the scanning-position single-member 2 or multiple-element transducer member 4, the switching combination of fixed-array beams 6 or any combination thereof. Preferably the location of ultrasound transducers is achieved through servo-movement.

Said ultrasonic beams can be accurately positioned via ultrasonic grid arrays or reference markers located on a device case or housing 7 or at any point within said beams as a measure of final beam-positioning feedback for high resolution and focus accuracy for said converging ultrasonic beams. The beam-positioning feedback enables the servo-control position circuitry 8, in turn, to reflect the positional requirement for said ultrasonic beams, either in accordance with an operators remote selection, by way of communication means, or locally selected by way of direct communication, input into said servo-control position circuitry through manipulation of ultrasonic beams 1 and focal point 5. Transducer members 4 may be adjusted so that the direction of the ultrasonic beams 1 can be oriented either two-dimensionally or three-dimensionally according to the positioning of at least one servo-adjust spigot 3. A secondary ultrasound member comprising a single transducer member, or alternatively at least two transducer elements, may comprise of either a single ultrasonic beam 2 or multi-array ultrasonic beams 4. Furthermore, multi-layer, multi-array ultrasonic beams may be used where a singular or group of three-dimensional (in space) positioning ultrasonic beam focus capability by way of aperture adjustment 11, such as piezo-aperture control.

As stated, the scope of the invention includes alternative embodiments to that herein illustrated and may include embodiments wherein the sound transducers are arranged in arrays and in multiple layers of arrays. Embodiments include those where the sound transducers are arranged in a single array, the sound beams generated by a plurality of transducers in an array focussed at a single target. The transducers in an array may be in fixed position or moveable.

The apparatus may include a fiducial registration means (not shown) for maintaining the optimal positioning of sound-emitting elements for continued sonication when the subject moves, for example. Preferably said fiducial registration means are additional sensors attached to ultrasonic transducers and transceiver devices attached to a subject. Communication between fiducial registration means way be through wire connectors or wireless communication means. Said fiducial registration means includes means for attachment to the subject and means for communicating between the subject and the servo-control means 8. The control means includes means to measure the correct registration of signals from the fiducial registration means. The fiducial registration means is placed in fixed position at the commencement of sonication with a suitable adhesive material such as self-adhesive locators attached to a subject. When the communication between the fiducial registration means and the control means indicate a departure from the initial optimal signal registration; the control system may prompt the operator by way of a prompting means that the sound-emitting means is out of alignment. Said prompting may occur automatically. Such a method and device enhances the ultrasonic beam targeting method, where for example, a subject ultrasonic transducer attachment device, such as one located on glasses or a headcap, moves during automatic or remote-controlled recanalisation or sonication of the subject.

The invention includes that the variability of velocity of ultrasound waves in different tissues may be exploited to characterise the tissues in a region of interest in a subject where it is suspected that there might be an occlusion or a restriction in fluid flow, for example, blood flow. Sonicating a region of interest with multiple frequencies of sound-wave beams, each selected frequency being associated with a tissue type as indicated in FIG. 2b, wherein the multiple frequencies are generated by any of at least one sound-emitting element at spaced intervals or two or more sound-emitting elements concurrently or in a pre-determined series of frequencies allows the characterisation of an occlusion or restriction in fluid flow as being attributable to a cause such as a gas bubble or bubbles, solid material, blood, tissue, vessel, skin, organs or other material.

The invention includes an apparatus having an arrangement of ultrasound transducers that enables the automatic mapping or visualisation of the progress of the dissolution of the target embolus.

The invention includes means capable of servo-feedback to ultrasonic turbulence (such as fast Fourier transformation) representation of the turbulence associated with blood vessel occlusion. Preferably the servo-feedback is optimised for the most effective vessel recanalisation.

The invention advantageously utilises sound waves produced by an ultrasound transducer to locate blood vessels that might show embolism. One embodiment of the invention includes a method for identifying an embolism or stenosis. In a first step of said method, regions of the body in which emboli might be found are identified. Preferably the region of the body is the head. More preferably the region of the body is the circle of Willis in the head. In a second step, a particular region of interest is selected. In a third step parameters of flow and turbulence are calculated for subsequent automatic ultrasound beam localisation in a fourth step, said parameters including the spectral power or amplitudes or phase coupling or frequency segmented characteristics of flow and turbulence of flow blood.

In said first step of identifying regions of the body in which emboli might be found, at least one ultrasound transducer generates an ultrasound beam which is moved across the surface of the region of the body in a scanning motion. Said ultrasound transducer or transducers may be fixed in an array in space relatively to one another or moveable in space relative to one another. Alternatively, said transducers may be fixed in arrays in layers. Said beams from said ultrasound transducers in said scanning motion may be operated in said scanning motion either simultaneously or sequentially across said body regions.

In the second stop the Doppler effect on echo beams received by the transducers is calculated. The analysis characterises the flow characteristics associated with the variation in frequency detected from the original ultrasonic transmission beam frequency. The analysis incorporates referencing and compensating for beam signals associated with normal echo beams such as flows associated with heart pumping or respiration and distinguishes such echo beams from beam signals of interest. The analysis further incorporates compensating for beam signals such as those associated with flow artefacts associated with ghost echoes, and those attributable to partial flows around occlusions and/or locally enhanced flows near occlusions.

Said ultrasound transducers generating the pulsed or unpulsed ultrasound beams may also receive the transmitted return echoes of transmitted beams. Where ultrasound beams are transmitted from a transducer in a continuous, i.e. unpulsed wave, a beam is initially transmitted with a first frequency or amplitude and subsequently with periodic changes resulting a second and further frequency or frequencies or amplitude(s) relative to the first beam frequency so that the mark-to-space ratio of the changing (apparent) pulse formation (but continuous) enables the computation of distance by decoding and determining the received (apparent) pulse from the last or a specific transmission pulse (known from the changes-amplitude, frequency; phase or any combination thereof characteristics in the second and later characteristics of the continuous beam, known receive time and known speed of beam enables distance calculation related to reflected beam and Doppler shifted return pulse, for example).

The changes in frequency based upon the principles of Doppler frequency modification provide a composited signal comprised of various blood flow characteristics associated with said scanning beam. Contained within said composited signal is a range of data which may be extracted by means of frequency power and frequency segment characterisation.

Preferably the sound waves generated by an ultrasound-emitting element are within the ultrasound frequency range. It will be understood that the invention is not restricted to an apparatus or method comprising ultrasound waves, but that an apparatus or method according to the invention can accommodate frequency bands other than those within the ultrasound frequency band.

Frequency power or amplitude spectral analysis can be conducted using same or similar means to Fast Fourier Transform, whereupon various components of the flow and flow turbulence signals associated with said ultrasound beam are represented in terms of power or amplitude of each respective frequency or range of frequencies of said beams. The frequencies or range of frequencies in turn represent the various changes or modifications through the Doppler principle of the original transmission ultrasonic beam. In turn the combination or characteristic "fingerprint" of the combinations of frequency power and absolute frequencies present provide an indication of Suspicious Regions of Interest (SROI) wherein an embolism might be located.

For the desirable target scanning and detection of SROI certain properties will be detected in a sequence of more and more sensitive scans, conducted in a spatial voxelated (3D spatial biological substance segmented into triangular voxels each associated to a mathematical matrix to enable recall with spatial localisation of x, y, z coordinates) visualisation (means to represent said voxels into an image or image view or travel path through said biological subject) until the most sensitive scan sequence is conducted and the subsequent SROI also marked.

The properties of the characteristics or "finger-prints" and the sequence of progressively more sensitive scans will determine the sensitivity and specificity of the present device and method for detection SROI in relation in particular to vessel occlusions.

The invention includes that the unique combination of blood flow or absolute and specific frequency of the blood and the spectral power enables a determination of the location of a specific occlusion and a determination of the nature of the material causing the occlusion.

The invention includes a method that utilises such characteristics and associated determinations to firstly, detect the spatial location of such occlusions and, secondly, determine the specific location of the occluding material in order to determine where to direct the ultrasonic beam to assist with the agitation or dissipation of such an occlusion to advantageously be most effective in eliminating or reducing the occlusions. Similarly, the beams can be directed in such a manner that the paths or trajectory of the beams provide minimal power and energy transfer to healthy cells but the focus or combined beams enhance the ability to diffuse of break-up such blockage material, in the fastest but safe manner.

The invention includes apparatus and methods for focussing a plurality of beams of ultrasound waves with the concentration of said beams causing the agitation or dissipation of an occlusion in a blood vessel.

The invention includes apparatus that generates ultrasound waves and measures the Doppler effect on reflected waves in a stable manner. In operation the apparatus scans the target areas of the body for known spatial flow characteristics of relatively strong and distinct blood vessels. The locational map of the spatial characteristics or a simplified syntactic representation of the blood vessel spatial characteristics are stored in memory, in particular, specific coordinates that respond to certain known vessel location properties.

By utilising a biological referencing system said apparatus or method can periodically check the movement of the apparatus against said biological reference point and appropriately adjust the display or data coordinates in accordance to the compensation of such detected movement. This enables an operator to continue to read and view relatively stable readings, data or image display. Also the servo mechanisms of the apparatus can compensate for the movement of the apparatus during operation and continue to treat or diagnose the selected areas or regions of interest.

The method includes the use of Doppler signal data to calculate parameters associated with fluid flow, including the speed, volume, and intensity of flow. This includes the ability to determine the rate of change in any parameter over time. By calculating these parameters at spaced intervals and calculating the differences in the parameters over the intervals the progress of dissipation of an occlusion or recanalisation of a restriction may be conveniently measured. The changes in the parameters can be conveniently used to determine the effectiveness of the sonication procedure, in particular, that the procedure has effectively dissipated an occlusion or recanalised a restriction so that the cause of the reduced fluid flow has been removed substantially from the vessel. In particular, the rate of change of any parameter may be included in the calculation of any index, marker, measure, or representation of the progress of the sonication.

Figure 7:
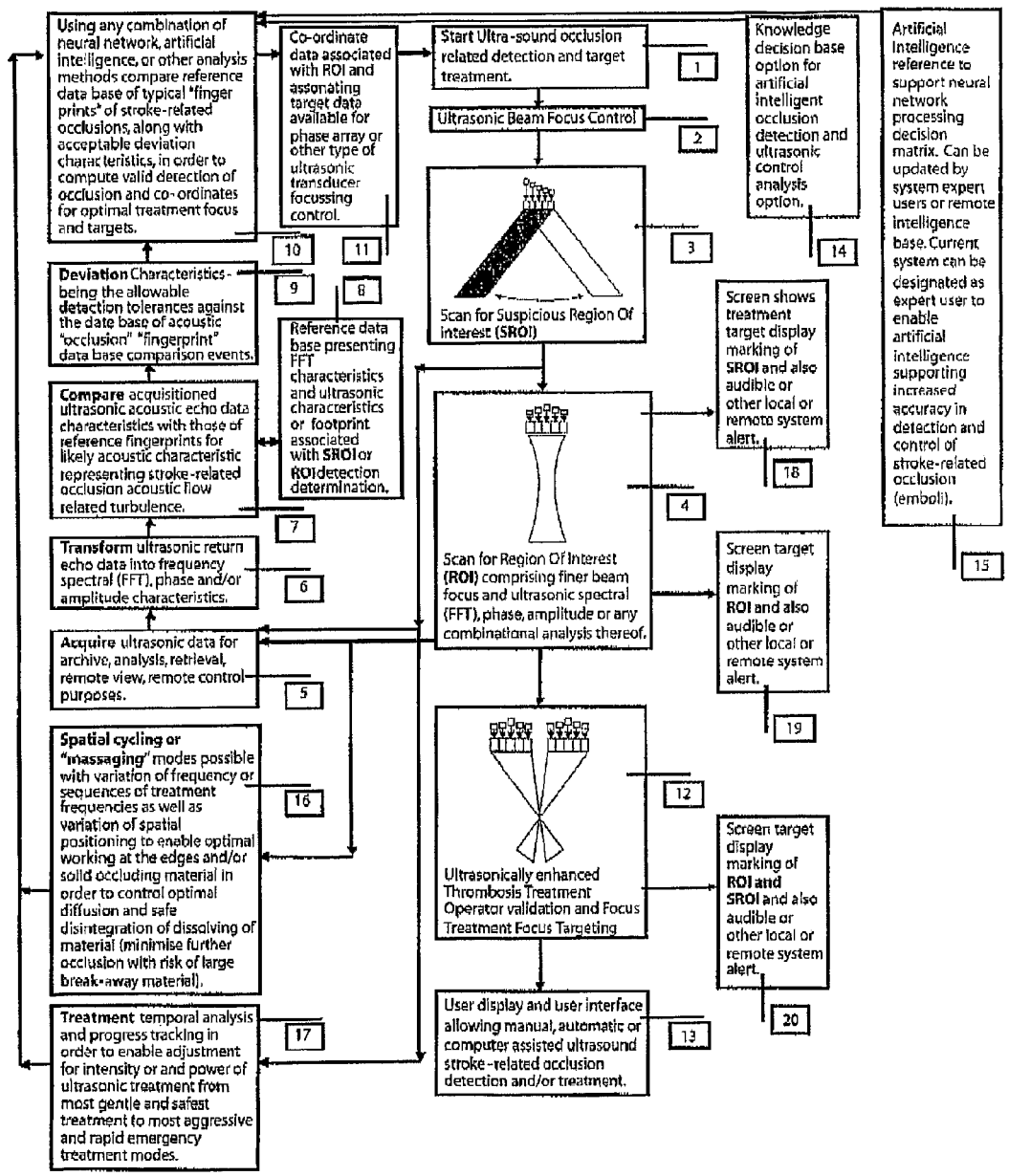
FIG. 7 shows an embodiment of invention in a sequence of operation of a phased array of ultrasound transducers.

FIG. 7 shows a typical sequence of operation of an embodiment of the invention in apparatus and method for identifying and sonication a thrombosis in the following sequence of steps, wherein the number of the step below is indicated at its corresponding place in FIG. 7.

1. Start ultra-sound occlusion-related detection and target treatment.
2. Ultrasonic Beam Focus Control.
3. Scan for Suspicious Region Of interest (SROI). The Doppler stroke-treatment ultrasound phased-array transducers can be steered across larger regions to enable a means to scan for SROI.
4. Once the SROI candidate(s) are detected the finer resolution focus mode can be applied to determine the Region Of Interest (ROI). The ROI as with SROI can be subjected to further FFT or acoustic footprint analysis, characterisation and comparison (with deviation consideration) and final operator verification.
5. Scan for ROI comprising finer beam focus and ultrasonic spectral (FFT), phase, amplitude or any combinational analysis thereof. FFT spectral "foot-print" or acoustic characteristic footprint, associated with occlusion blood flow can be detected firstly on the course scan and detect mode [SROI] Acquire ultrasonic data for archives analysis, retrieval, remote view, remote control purposes.
6. Transform ultrasonic return echo data into frequency spectral (FFT), phase and/or amplitude characteristics. ROI can be detected by way of computing the acoustic or FFT foot print across a region using sweep mode and then utilisation representing characteristic of blood turbulence or flow characteristics associated with vascular partial or total occlusion.
7. Compare acquisitioned ultrasonic acoustic echo data characteristics with those of reference fingerprints for likely acoustic characteristic representing stroke-related occlusion acoustic flow related turbulence.
8. Reference data base presenting FFT characteristics and ultrasonic characteristics or footprint associated with SROI or ROI detection determination.
9. Deviation Characteristics—being the allowable detection tolerances against the data base of acoustic "occlusion" "fingerprint" data base comparison events.
10. Using any combination of neural network, artificial intelligence, or other analysis methods compare reference data base of typical "finger-prints" of stroke-related occlusions, along with acceptable deviation characteristics, in order to compute valid detection of occlusion and co-ordinates for optimal treatment focus and targets.
11. Co-ordinate data associated with ROI and assonating target data available for phase array or other type of ultrasonic transducer focussing control.
12. Ultrasonically enhanced Thrombosis Treatment Operator validation and Focus Treatment Focus Targeting.
13. Once operator verification is acknowledged user can select to automatically lock in ultrasonic-enhanced thrombosis mode, where upon phase array multiple beam focus treatment can be applied.
14. User display and user interface allowing manual, automatic or computer assisted ultrasound stroke-related occlusion detection and/or treatment.
15. Knowledge decision base option for artificial intelligent occlusion detection and ultrasonic control analysis option. Artificial Intelligence reference to support neural network processing decision matrix. Can be updated by system expert users or remote intelligence base. Current system can be designated as expert user to enable artificial intelligence supporting increased accuracy in detection and control of stroke-related occlusion (emboli).
16. Spatial cycling or "massaging" modes possible with variation of frequency or sequences of treatment frequencies as well as variation of spatial positioning to enable optimal working at the edges and/or solid occluding material in order to control optimal diffusion and safe agitation or dissipation of dissolving of material (minimise further occlusion with risk of large breakaway material).
17. Treatment temporal analysis and progress tracking in order to enable adjustment for intensity or and power of ultrasonic treatment from most gentle and safest treatment to must aggressive and rapid emergency treatment modes.
18. Screen shows treatment target display marking of SROI and also audible or other local or remote system alert.
19. Screen target display marking of ROI and also audible or other local or remote system alert.
20. Screen target display marking of ROI and SROI and also audible or other local or remote system alert.

The invention includes apparatus having remote video capabilities for observing the output of ultrasound beam is generated from an ultrasound transducer at a location remote to the subject on which the beams are focussed.

The apparatus include the possibility of remote manual adjustment to the control on ultrasound beam parameters.

The apparatus may include a three-dimensional bio-optical means wherein the ultrasound signal received by an ultrasound transducer is transformed into computer graphics for easy viewing and interpretation by an operator.

The apparatus may include a method for transforming TCD output signals into graphical representations for a computer or other viewing screen. It will be understood that the screen may be any screen capable of displaying a digital or analogue signal.

The invention includes an array of ultrasound-emitting elements wherein each element of said array is capable of focussing ultrasound waves at a focal point. The invention includes ultrasound elements that are piezo-electric crystals in an ultrasound transducer.

The invention may include apparatus operable with voice coil technology for the positioning of ultrasound transducers on a patient's head.

The invention includes an apparatus for TCD ultrasound that automatically or semi-automatically scans and maps the location of blood vessel occlusions, using the methods described herein. Said automatic or semi-automatic mapping is effected by the use of means, such as a computer database and program or programs in which normalitive sound-wave data is stored for automatic comparison with sound-wave data acquired from the sonication of an SROI or ROI according to the procedure illustrated in FIG. 7. Said database may contain data representative of a two-dimensional or three-dimensional map for the SROI or ROI in a subject or a representative normalised subject. Said means may further include computer program or programs for displaying representations of the acquired data in comparison with normalitive data, such as on a video display unit. Said computer program or programs may suitable processing techniques for reflected ultrasound waves such as fast Fourier transformation techniques, and determining the most likely regions for occlusions by comparing fast Fourier outputs for free-flowing or occluded vessels. Said video display unit may show a representation of the region being sonicated, preferably in real-time according to the information stored in the database. Said computer program may further display acquired sonication data on said video display unit to indicate the position of sonication in two-dimensional or three-dimensional space in relation to known anatomical characteristics of a subject.

The method of the invention includes a diagnostic capability to detect an occlusion either by way of the measurement of fluid flow in a ROI or turbulence in the vicinity of an occlusion. Said diagnostic capability may include a comparison of sound-wave data indicating the presence of fluid spurts within a vessel or fluid flow rates associated with recanalisation of stenosis in such a way as to enable the distinction between the presence of an occlusion or a stenosis. Said diagnostic capability includes the calculation of fluid flow and turbulence in the region of the occlusion or stenosis by way of using sound-wave data for measurement of any of fluid flow rate, fluid flow quantity, fluid turbulence, or intensity.

The apparatus or method further includes displaying an index, measure, marker, or series of markers or other suitable representation characteristic of the progress of recanalisation of a vessel during any or both of diagnosis or treatment on said video display unit. The apparatus or method further may include the incorporation of said index, measure, or series of markers into a means, such as a computer program, for optimising the at least one sound-wave beam incorporating at least one frequency in order to provide better control over the rate of recanalisation and sonication power.

The invention includes many embodiments. For example, the invention includes apparatus wherein a first ultrasound transducer is fixed in relation to a target occlusion characteristic of embolism in a blood vessel. A second ultrasound transducer is positioned in relation to said first transducer such that both transducers focus the emitted beams of ultrasound waves onto an occlusion in said blood vessel. The second transducer may be positioned using a servo device. It will be apparent to those skilled in the art that more than two ultrasound transducers may be included in the invention and that each transducer may be positioned relative to the others so that the target occlusion is located at a common focal point for the beams of ultrasound waves. Preferably the invention includes an array of transducers. Preferably the array is a structured array. The advantageous effect of the multiple ultrasound transducers with a common focal point will be to focus the maximum ultrasound energy on the occlusion and result in the most effective embolism dispersing treatment.

The invention provides a method to optimise the focus of the ultrasound beam or beams using servo-movement. One or more servo mechanisms and/or ultrasonic phased array transducer control systems can be deployed to enable a continuously variable positioning of focus point in order to enable optimal energy focus of one or more beams. The said energy focus is able to be divided at one or more precise locations with high spatial resolution in order to focus energy away from healthy tissue (is desirable and as desirable), where at the same time focussing energy of a set of beams at the location of vascular occluding material, in order to disintegrate or diffuse or disperse said occluding material in an optimal and safe treatment manner.

Furthermore, the at least one treatment beam of ultrasonic frequency can comprise one or more frequencies optimized for functions enabling any sequence or simultaneous combination of optimal a) gaseous partial or total occlusive material detection; b) solid material partial or total occlusive material detection; or c) gaseous partial or total thrombolysis and recanalisation of partial or fully occluded blood vessels.

The invention provides an apparatus and method to facilitate the safe dispersion or dissolving of an occlusion (thrombolysis or recanalisation of blood vessel). One of the risks associated with ultrasonically enhanced thrombolysis is the risk that dislodged occluding material can "break away" or disintegrate in large and unsafe particle sizes, which in turn can cause further occlusion or risks of occlusion or partial vessel blockages. In particular, vessel blockages such as within the legs or lower body may be recanalised and cause particles to travel higher in the circulatory system such as in the brain. In these regions the vessels can be smaller and lead to further blockages and more serious consequences such as ischaemic stroke.

The invention provides an apparatus and method for simultaneous diagnosis and treatment to regulate towards safe thromobolysis and recanalisation of blood vessels. The present invention includes the diagnosis or identification of a particle or total occlusion of a vessel while at the same time or separately providing ultrasonically enhanced thrombolysis or vessel recanalisation.

The focus adjustment and targeting of the at least one ultrasonic beam, along with accurate spatial resolution and power control (of targeted ultrasound treatment) enables a controlled dispersion of occluding material in a vessel by allowing different patterns or massaging (movement of beam focus around, over and near occluding material) and different ultrasonic frequencies or combination or sequences of frequencies (different frequencies effect different material types and also effect the dispersion rate and size of dispersed occluding material particles) or any combination thereof to be applied to the region of vessel occlusion or partial occlusion. The treatment of an occluded vessel can thus be controlled, targeted and regulated in order to minimize the particle dispersion size and risk for further occlusion.

The present invention enables one or more ultrasonic frequencies either sequentially or simultaneously to be generated as a means to both enhance diagnosis and imaging and also enhance ultrasonic vessel recanalisation treatment.

The present invention includes a three-dimensional mapping capability and tracking of the maximum power generation by the at least one ultrasound transducer. This enables a register or matrix representing the computation of ultrasonic power generation at any point in time and any spatial location under scan. Said "matrix or register" computes the probable power dissipation of ultrasound scan beams based on the beam dispersion characteristics. Furthermore, the intersection of beams along with the focus characteristics are computed and provide a resulting reference data set to enable or to ensure that maximal safe power thresholds are achieved at all locations and that the additional ultrasonic power required to rapidly diffuse vessel occlusion is only directed specifically where required and where safe, i.e., targeted at surrounding healthy tissues.

The present invention provides the capability to enable ultrasonically-enhanced thrombolysis and vessel recanalisation to be moderated in treatment intensity (power) in accordance with or in harmony with "clot-busting drug" characteristics of action. This consideration can minimize risk of side effects of each said treatment, such as haemorrhage risk with "clot-busting drug" treatment, or excessive ultrasound power and cell harm with ultrasound treatment.

The present invention provides that data such as the drug administration rate, drug composition or type, and patient risk category to haemorrhage, such as haemophiliacs, can be entered into a clot drug-profusion device and also ultrasound power and focus control, for example.

The present invention most advantageously enables the intravenous or manual administration of clot-busting drugs to be regulated or monitored in such a manner as to regulate the balance between the strength of the clot balanced or administration optimized to minimize the risk of side effects the occluding material and minimally targeted clot-busting drug administration, with risks of haemorrhage side effects, with the aggressive or high powered application of ultrasonically enhanced thrombosis treatment, with the risk of healthy cell harm and also dispersion of further clot-causing material.

The present invention enables the ultrasonic control and the "clot-busting drug" administration to be servo-controlled in such a manner that optimal speed of thrombosis and recanalisation of the vessel(s) and also optimal safety or mitigation to patient risks are possible.

REFERENCES

Alexandrov, A V. 2002. *European J Ultrasound* 16: 131-140. Ultrasound-enhanced thrombolysis for stroke: clinical significance.

Alexandrov, A V. Molina, C A., Grotta, J C., Garami, Z., Ford, S R., Alvarez-Sabin, J., Montaner, J., Saqqur, M., Demchuk, A M., Moyé, L A., Hill, M D., and Wojner, A W. 2004. *New England J Medicine*. 351: 2170-2178. Ultrasound-enhanced systemic thrombolysis for acute ischemic stroke.

Demchuk, A M, Burgin, W S, Cristou, I., Felberg, R A, Barber, P A, Hill M D, Alexandrov A V. 2001. *Stroke* 32: 89-93. Thrombolysis in brain ischemia.

Tegeler, C H, and Ratanakorn, D. 1999. "Physics and Principles". In *Transcranial Doppler Ultrasonography*, Bibikian, V L., Wechsler, L R, Toole, J F. Eds., Butterworth Heinemann, Melbourne. pp 3-11.

The invention claimed is:

1. Apparatus for imaging or treatment of occlusions or restrictions in vessels using sound waves, comprising:
    at least one servo-controlled sound transducer member including at least one sound-emitting element for producing at least one sound wave beam, the sound transducer member controlled by a feedback control signal originating from an occlusion in fluid flow, a restriction in fluid flow, or a combination thereof;
    means to adjust the parameters of said at least one sound wave beam for imaging or treatment of occlusions or restrictions in vessels;
    means to spatially locate said at least one sound-emitting element;
    means to automatically or semi-automatically focus sound waves generated by said at least one sound-emitting element into a beam; and
    means to accept sound signals from sound-emitting element or elements.

2. Apparatus according to claim 1 including means to move said at least one transducer member.

3. Apparatus according to claim 2 including means to control movement of said at least one transducer member automatically or semi-automatically.

4. Apparatus according to claim 1 wherein the sound-emitting element and the means to accept sound signals are the same.

5. Apparatus according to claim 1 wherein the at least one sound wave beam is pulsed.

6. Apparatus according to claim 1 wherein the at least one sound wave beam is focussed electronically.

7. Apparatus according to claim 1 wherein the at least one sound-emitting element is a plurality of sound-emitting elements forming an array.

8. Apparatus according to claim 7 wherein the array is curved.

9. Apparatus according to claim 7 wherein the at least one sound wave beam incorporates a plurality of frequencies of sound waves in combinations of concurrent frequencies generated by the sound-emitting elements in the array or in series of frequencies over time.

10. Apparatus according to claim 7 wherein the array of sound-emitting elements is located in a fixed position, adjustable position, or scanning position.

11. Apparatus according to claim 7 further including a plurality of sound-emitting elements in at least two layers of at least two arrays.

12. Apparatus according to claim 1 wherein the sound-emitting elements are moveable singly, in a coordinated manner, or in a simultaneous coordinated manner.

13. Apparatus according to claim 1 including means to transform a sound signal from analogue to digital forms or digital to analogue forms.

14. Apparatus according to claim 1 including means to store transformed digital data.

15. Apparatus according to claim 1 including means to display analogue or digital data.

16. Apparatus according to claim 15 including video display means for displaying the analogue or digital data or indicating to an operator of the status of the sonication.

17. Apparatus according to claim 1 including voice coil control means for controlling the sound transducer member.

18. Apparatus according to claim 1 wherein said apparatus is operable in real-time or near real-time.

19. Apparatus according to claim 1 for use in detecting and sonicating vessels in the brain of a subject.

20. Apparatus according to claim 1 wherein the sound waves are ultrasound waves.

21. Apparatus for imaging or treatment of occlusions or restrictions in vessels using sound waves, comprising:
at least one servo-controlled sound transducer member including at least one sound-emitting element for producing at least one sound wave beam, the sound transducer member controlled by a feedback control signal originating from an occlusion in fluid flow, a restriction in fluid flow, or a combination thereof;
means to adjust the parameters of said at least one sound wave beam for imaging or treatment of occlusions or restrictions in vessels;
means to orient said at least one transducer member;
means to focus sound waves generated by said sound-emitting element into a beam; and
means to accept sound signals from sound-emitting element or elements.

22. Apparatus according to claim 21 wherein the servo-controlled sound transducer member is self-tracking and including means for determining out-of-range positioning of said at least one sound-emitting element.

23. Apparatus according to claim 21 wherein each transducer member is operable to enable a continuously adjustable focus point comprising of two or more sound wave beams emitted by at least two sound-emitting elements.

24. Apparatus according to claim 21 including fiducial registration means for maintaining targeted sonication, said fiducial registration means in communication with the sound transducer member.

25. Apparatus according to claim 24 including means for prompting an operator when said apparatus is out of registration.

26. Apparatus according to claim 24 wherein the communication is effected wirelessly.

27. Method for locating an occlusion in a vessel or a restriction in a vessel, including the steps of:
identifying regions of a body in which an occlusion or restriction might be found;
selecting a region of interest for sonication with sound waves;
sonicating the region of interest with at least one sound-wave beam produced by a servo-controlled sound transducer member by moving said sound-wave beam across said region of interest;
receiving reflected sound signals from said region of interest, wherein at least one of said sound signals is a feedback control signal originating from an occlusion in fluid flow, a restriction in fluid flow, or a combination thereof, wherein the sound transducer member is responsive to the feedback control signal; and
calculating the Doppler effect parameters of flow and turbulence from said reflected sound signals.

28. The method according to claim 27 including the step of modifying the characteristics of the at least one sound-wave beam to target a region of interest wherein the Doppler effect parameters are indicative of reduced flow attributable to an occlusion or a vessel restriction.

29. The method according to claim 27 wherein the region of the body is the head.

30. The method according to claim 29 wherein the region of the head is the circle of Willis.

31. The method according to claim 27 wherein two or more sound-wave beams are moved across said region of interest in either a simultaneous or sequential manner.

32. The method according to claim 27 wherein the at least one sound-wave beam is pulsed.

33. The method according to claim 27 wherein the parameters calculated from said reflected sound signals are any one or a combination of power, spectral, amplitude, phase coupling or frequency characteristics characteristic of a spatial representation of anatomical features in said region of interest or occlusive material.

34. The method according to claim 33 wherein an analysis of the power, amplitude or spectral characteristics are carried out using Fast Fourier Transform techniques.

35. The method according to claim 33 including the step of comparing calculated parameters with known parameters of anatomical features in said region of interest.

36. The method according to claim 27 wherein the at least one sound wave beam is continuous.

37. The method according to claim 36 wherein the at least one sound wave beam is initially transmitted with a first frequency or amplitude and subsequently transmitted with periodic changes resulting in a second and further frequency or frequencies or amplitude(s) relative to the first beam frequency maintaining the mark-to-space ratio of the apparent changing and pulse formation.

38. The method according to claim 27 wherein the sound-wave beam is comprised of ultrasound waves.

39. The method according to claim 27 including the step of conducting a spatial voxelated analysis of received signals.

40. The method according to claim 27 wherein the steps are carried out automatically or semi-automatically substantially without human control.

41. Method for distinguishing anatomical features of an organism including the steps of:
sonicating a region of the body of said organism with at least one sound-wave beam produced by a servo-controlled sound transducer member;
whereby the frequency of said at least one sound-wave beam is suitable for determining a particular tissue type;
receiving reflected sound signals from said region of interest, at least one of said sound signals is a feedback control signal originating from an occlusion in fluid flow, a restriction in fluid flow, or a combination thereof, wherein the sound transducer member is responsive to the feedback control signal;
calculating the Doppler effect parameters of said reflected sound signals; and
characterising said Doppler effect parameters according to parameters associated with known tissue types.

42. The method according to claim 41 whereby a sound-wave frequency suitable for a particular tissue type is generated at spaced intervals with a different frequency suitable for a different tissue type.

43. The method according to claim 41 whereby at least two frequencies suitable for at least two tissue types are generated simultaneously.

44. The method according to claim 41 including the step of calculating any one or a combination of fluid flow rate, fluid flow quantity, or turbulence from said Doppler effect parameters.

45. The method according to claim 44 including the step of sonicating the region of interest thereby causing agitation or dissipation of the occlusion by prolonged sonication or recanalisation of a vessel restriction.

46. The method according to claim 45 including the step of automatically or semi-automatically evaluating and optimising the effect of sonication for feedback modification of said at least one sound-wave beam according to tissue safety guidelines.

47. The method according to claim 46 wherein the step of automatically or semi-automatically evaluating and optimising the effect of sonication includes maintaining a fiducial registration between sound-wave beams and a registration signal.

48. The method according to claim 47 including the step of indicating when the sound-wave beams are out of registration.

49. The method according to claim 45 including the step of calculating and displaying any one or a combination of an index, measure, or marker or suitable representation indicating the progress of dissipation of an occlusion in a vessel or recanalisation of a vessel having an occlusion or restriction using said Doppler effect parameters.

50. The method according to claim 49 including carrying out calculating and displaying the result of any calculation at spaced intervals.

* * * * *